United States Patent [19]
Rosenberger et al.

[11] Patent Number: 5,525,342
[45] Date of Patent: Jun. 11, 1996

US005525342A

[54] REOVIRUS STRAIN 2177 AND VACCINE CONTAINING SAME

[75] Inventors: John K. Rosenberger, Landenberg, Pa.; Donald E. Roessler, Lewes; Rudolf G. Hein, Georgetown, both of Del.

[73] Assignee: Akzo Nobel, N.V., Arnhem, Netherlands

[21] Appl. No.: 247,174

[22] Filed: May 20, 1994

[51] Int. Cl.$^6$ .................. A61K 39/295; A61K 39/15; A61K 39/255; A61K 39/215

[52] U.S. Cl. .................. 424/202.1; 424/215.1; 424/204.1; 424/214.1; 424/229.1; 424/222.1; 424/232.1; 435/235.1

[58] Field of Search .................. 424/202.1, 215.1, 424/214.1, 222.1, 229.1, 232.1; 435/235.1

[56] References Cited

PUBLICATIONS

Giambrone, J J et al, 1989, Poultry Science vol. 68 pp. 1213–1217.
Eidson, C. S. et al. 1983, Poultry Science vol. 62 pp. 1177–1188.
Giambrone, J J et al. 1991, Avian Diseases vol. 35 pp. 204–209.
Thayer, S. G. et al. 1983, Poultry Science vol. 62 pp. 1991–1997.
F. J. Sterner, "Role of Reovirus in an Apparent Malabsorption Syndrome–of Chickens," Thesis, University of Delaware, Aug., 1982.
C. L. Rinehart, "Interaction of the Avian Reoviruses with the Immune System of Chickens," Thesis, University of Delaware, Jun. 1984.
A. Margolin, "Clinical Evaluation of Broiler Chickens Infected with Several Reovirus Pathotypes," Thesis, University of Delaware, Aug., 1983.
D. E. Roessler, "Studies on the Pathogenicity and Persistence of Avian Reoviruses Pathotypes in Relation to Age Resistance and Immunosuppresion," Thesis, University of Delaware, Dec., 1986.
J. J. Biambrone, "Course Spray Application of Enterovax® in Day–Old SPF Broilers for the Prevention of Enteric Reovirus Infections," Proceedings of the Fourtyth Western Poultry Disease Conference, Acapulco, Mexico, Apr. 24–27, 1991.
V. S. Gouvea et al., "Polymorphism of the Migration of Double–Stranded RNA Genome Segments of Avian Reoviruses" *Journal of Virology*, 43:2:465–471, 1982.
D. E. Roessler et al., "In Vitro and In Vivo Characterization of Avian Reoviruses." *Avian Diseases*, 33:555–565, 1989.

J. K. Rosenberger et al., "In Vitro and In Vivo Characterization of Avian Reoviruses." *Avian Diseases*, 33:535–544, 1989.
J. K. Rosenberger et al., "Characterization of Reoviruses Associated with a Runting Syndrome in Chickens" *Disease Prevention and Control in Poultry Production*, Aug. 31–Sep. 2, 1983, Sydney, Australia.
R. D. Montgomery et al., "Persistence of Commercial Modified Live Reovirus Vaccines in Chicks," *Avian Diseases*, 32:461–468, 1988.
L. van der Heide et al., "Infectious Tenosynovitis (Viral Arthritis): Characterization of a Connecticut Viral Isolant as a Reovirus and Evidence of Viral Egg Transmission by Reovirus–Infected Broiler Breeders," *Avian Diseases*, 19:4:683–688, 1975.
A. H. Sharpe et al., "Reovirus Inhibition of Cellular DNA Synthesis: Role of the S1 Gen," *Journal of Virology*, 38:1:389–392, Apr., 1981.
L. van der Heide et al., "Development of Attenuated Apathogenic Reovirus Vaccine Against Viral Arthritis/Tenosynovitis", *Avian Diseases*, 27:3:698–706 1983.
R. K. Cross, "Reovirus–Specific Polypeptides: Analysis Using Discontinuous Gel Electrophoresis," *Journal of Virology*, 19:1:162–173, 1976.
D. R. K. Hieronymus et al., "Identification and Serologcal Differentation of Several Reovirus Strains Isolated from Chickens with Suspected Malabsorption Syndrome," *Avian Diseases*, 27:1:246–254, 1982.
G. Mandellie et al., "Experimental Reovirus Hepatitis in Newborn Chicks," *Vet. Pathol.*, 15:531–543 (1978).
R. C. Jones et al., "Characteristics of Reovirus Isolated From Ruptured Gastrocnemius Tendons of Chickens," *Veterinary Record*, Feb. 15, 1975.
R. K. Page et al., "Malabsorption Syndrome in Broiler Chickens," *Avian Diseases*, 26:3:618–624, 1980.
B. S. Bains et al., "Reovirus–Associated Mortality in Broiler Chickens," *Avian Diseases*, 18:3:472–476, 1974.
D. C. Johnson et al., "Incidence of Tenosynovitis in Maine Broilers," *Avian Diseases*, 829–834, 1971.
T. J. Bagust et al., "Isolation of Reoviruses Associated with Diseases of Chickens in Victoria", *Australian Veterinary Journal*, 51:406–407, Aug. 1975.
Rinehart et al, "Effects of Avian Reoviruses on the Immune Responses of Chickens," Abstract of Papers, pp. 1488–1489.

*Primary Examiner*—Mary E. Mosher
*Attorney, Agent, or Firm*—Mary E. Gormley

[57] ABSTRACT

Disclosed herein is the isolation of a relatively non-pathogenic reovirus, designated strain 2177, and vaccines comprising this strain.

17 Claims, No Drawings

REOVIRUS STRAIN 2177 AND VACCINE CONTAINING SAME

FIELD OF THE INVENTION

The present invention is directed to an apathogenic reovirus, designated strain 2177 and vaccines comprising strain 2177.

BACKGROUND OF THE INVENTION

Avian reoviruses have been associated with a wide variety of pathologies in commercial poultry. The most economically important reovirus disease is the arthritis/tenosynovitis syndrome. This condition is characterized by swelling of the tendon sheath of the metatarsus tendon immediately above the hock joint with resulting lameness of varying degrees. Gross swelling can result in reluctance of the chicken to move. The affected tendons can become firm and fibrotic, and adhesions to the tendon sheath and skin can result in a partially non-functional tendon [Johnson et al., *Avian Dis.* 15:829–834 (1971)]. Tendon rupture may occur in older birds [Jones et al., *Vet. Rec.*, 96:153–154 (1975)].

Reoviruses have also been associated with a syndrome called malabsorption or pale bird syndrome [Page et al., *Avian Dis.*, 26:618–624 (1982)]. This intestinal condition has been characterized by stunted growth, poor feathering, loss of pigmentation, enlargement of the proventriculus, enteritis, and leg weakness. The disease has been thought to be due to poor absorption of feed nutrients as a result of reovirus infection [Hieronymus et al., *Avian Dis.*, 27:246–254 (1983)].

Other pathologies thought to be caused by reoviruses are hepatitis, hydropericardium, ascites, pale kidneys, small spleens, pericarditis and myocarditis.

These conditions result in economic losses due to downgrading of broilers and poor performance in breeders which has been conservatively estimated at 15 million dollars per year.

Live vaccines in the United States have been developed from various passage levels of one arian reovirus strain, S1133, isolated and characterized by van der Heide from a field case of tenosynovitis. The strain was grown serially 235 times in the chorioallantoic membrane (CAM) at 37° C. and then 65 times in chicken embryo fibroblast (CEF) at 32° C. An additional 135 passages were carried out at 37° C. in CEF [van der Heide et al., *Avian Dis.*, 27:698–706 (1983)].

Current vaccination programs in breeders recommend vaccinating chickens at young age (7–14 days) with a mild vaccine derived from a high passage S1133, a live vaccination at 6–11 weeks of age with a slightly more virulent S1133 vaccine virus derived from a lower passage, with possibly a third live vaccination with the same slightly more virulent S1133 vaccine, followed by vaccination with killed products.

In broilers, vaccination is also performed as young as possible with a mild vaccine.

Vaccination at 1-day of age is not recommended with current vaccines due to the possibility of interference of reovirus with Marek's vaccination. Interference with Marek's vaccine has prevented the administration of the known reovirus vaccines at the same time as other immunizations, and has required a second series of vaccinations. Rosenberger, J. K., *Western Poultry Disease Conference Proceedings*, pp. 50–51, (1983).

Moreover, current vaccines have been found to persist in the tendon of vaccinates (Montgomery, R. D. and Maslin, W. R., *Avian Dis.*, Vol. 32, pp. 461–468, 1988) with the potential to multiply and cause arthritis or other leg problems as well as to be transmitted through the egg to the offspring.

An ideal vaccine would be one which is nonpathogenic, which would not persist in the chicken and which will not interfere with Marek's vaccines and thus could be administered at 1-day of age.

SUMMARY OF THE INVENTION

A new strain of avian reovirus has now been found, which was isolated from chickens with reovirus disease. This new virus was deposited with the ATCC, Rockville, Md., U.S.A. on Mar. 10, 1994, and assigned Accession Number VR 2449. A characteristic property of this virus is that it is apathogenic, and that when it is inoculated into chickens it provides protection against pathogenic strains of reoviruses.

In view of this discovery, according to the present invention, a vaccine is provided for the protection of poultry against pathologies caused by reoviruses, wherein the vaccine comprises reovirus strain 2177. The present invention is also directed to the isolated strain 2177, which has been found to be essentially non-pathogenic, does not persist in poultry that are inoculated with the strain, and which can be administered at a young age (e.g., one day of age).

The vaccine of the present invention may include strain 2177 alone or in combination with other viral vaccines of poultry, such as those for Marek's Disease Virus, Infectious Bursal Disease Virus, Newcastle Disease Virus, Infectious Bronchitis Virus, Avian Encephalomyelitis Virus, Fowl Pox Virus and Chicken Anemia Agent.

DETAILED DESCRIPTION OF THE INVENTION

Rosenberger disclosed the isolation of one hundred and nine reovirus isolates from young commercially-reared broilers afflicted with a condition characterized primarily by femoral head necrosis and inflammation of the hock joints (*Proc. Internatl. Union of Immunol. Soc.*, No. 66, Disease Prevention and Control in Poultry Production, Sydney NSW, Australia Aug. 31–Sep. 2, 1983). Virus isolations were accomplished by inoculation of 5- to 7-day-old embryonated eggs via the yolk sac with leg joint swabbings and with homogenized tissues (bone marrow, liver, spleen, and tendons) from clinically affected chickens varying in age from 1-day-old to approximately 4-weeks of age. Reovirus isolates were identified in the inoculated embryos by harvesting the chorioallantoic membranes from embryos that died and demonstrating the presence of the group specific reovirus antigen. The yolk, which contained reovirus, was collected, diluted in tryptose phosphate broth and stored at −70° C.

The one hundred and nine reovirus isolates were screened for pathogenicity by inoculating susceptible 1-day-old broiler chickens via the footpad route. Eleven of the isolates produced inflammation of the footpad and other portions of the leg between 3 and 14 days post-inoculation. These eleven isolates were selected for further studies.

The yolk seed pools of these eleven isolates were inoculated onto primary chicken embryo fibroblasts (CEF). One isolate (isolate 2177) was found to be incapable of producing any cytopathic effect when inoculated onto CEF. This virus was then passaged repeatedly (14 times) until cytopathology was observed. Cells and cell culture fluids were collected, frozen and thawed, clarified by centrifugation, and the supernatant containing the 2177 reovirus isolate adapted for growth in CEF was aliquoted and stored at −70° C.

The cell culture adapted reovirus 2177 was propagated in CEF cell cultures using a standard plaque assay system. The virus was plaque purified by individual plaque selection. The plaque purified reovirus 2177 was inoculated into the yolk sac of 6-day-old embryonated chicken eggs. Yolk was collected from embryos that died 24 hours or more post-inoculation and used as purified working stock of reovirus 2177.

This purified cloned 2177 reovirus was characterized in vitro and in vivo for genetic characteristics and pathogenicity in chickens. Generally, the 2177 reovirus was found to be essentially non-pathogenic in chickens. This makes this viral strain ideal for use as a live vaccine.

Vaccines according to the present invention comprise the 2177 virus in either live, attenuated or inactivated form. However, preferably the vaccine contains live virus; because of its nonpathogenicity, attenuation or inactivation are not necessary.

For the preparation of the live vaccine, the seed virus (prepared by 14 passages in CEF followed by 5 to 6 passages in chicken embryos) can be grown in cell culture, for instance CEF culture or other mammalian cell cultures (e.g., VERO cells), or in embryonated eggs. The virus thus grown can be harvested by collecting the tissue culture fluids and/or cells, or from the tissues or fluids of the embryonated eggs. The live vaccine may be prepared in the form of a suspension or may be lyophilized. The suspension form may be stored frozen. In the lyophilized form, it is preferable to add one or more stabilizers. Suitable stabilizers include, for example, carbohydrates (such as sorbitol, mannitol, starch, sucrose, dextran, glucose), proteins (such as albumin or casein) or degradation products thereof, and buffers (such as alkali metal phosphates). Optionally, one or more compounds having adjuvant activity may be added as well. Any conventional stabilizers and adjuvants may be included in a vaccine according to this invention.

For either the lyophilized form or the suspension form of the vaccine, the vaccines may be formulated of the cell culture medium from which the virus is obtained, which would include the virus, fetal, newborn or calf serum and antibiotics. The type of cell culture medium employed is not limited and may be any media and supplements conventionally used for the cell culture in which the virus is grown. The lyophilized formulations would further comprise the virus and stabilizers, alone or in combination with the media supplements, as mentioned above. A vaccine containing inactivated virus can, for example, comprise the cell culture medium containing the virus, fetal, newborn or calf serum, antibiotics, in an oil emulsion or tocol emulsion formulation.

Vaccination can be performed at any age. Normally, vaccination would occur at up to 12 weeks of age for the live product and between 14–18 weeks for the inactivated vaccine. For in ovo vaccination, vaccination would be done in the last quarter of embryo development. The vaccine many be administered subcutaneously, by spray, orally, intraocularly, intratracheally, nasally or in ovo. Preferably, chickens are vaccinated at one day of age. Older chickens appear to develop age resistance; but breeder chickens can still be vaccinated at, for example, 8 and 30 weeks (2 inoculations). It has been found that inoculation with 2177 produces no persistent virus and there is no vertical transmission to progeny. On the other hand, strain S1133 is passed to progeny.

Generally, the titer of the 2177 virus in the vaccine can be 1.0 to 9.0 log base 10 $TCID_{50}$ per dose; more preferably, the titer is 2.0 to 7.5 per dose; most preferably, the virus titer is about 4.0 log base 10 $TCID_{50}$ per dose.

One of the unique features of vaccines comprising the 2177 strain is that it can be combined to form a multivalent vaccine with other viruses, even other reoviruses, without causing interference. This is unique among reoviruses, which have been shown to interfere with the activity of other viruses in vaccines. This has been a particular problem with Marek's disease vaccines. See, e.g., *Poultry Science*, Vol. 62:1488, 1983. The 2177 virus can be combined with the following vaccine formulations: (a) all three serotypes of Marek's Disease vaccines: serotype 1 (e.g., CVI988); serotype 2 (e.g., SB-1); and serotype 3 (HVT); (b) Infectious Bursal Disease Virus (IBDV vaccines): classical strains (e.g., D78); Delaware variants (e.g., variant E, 89-03); and other variants (e.g., GLS); (c) both Marek's Disease and IBDV vaccines; (d) Newcastle Disease Virus (NDV)/Infectious Bronchitis Virus (IBV) vaccines; (e) Avian Encephalomyelitis (AE); (f) Fowl Pox; and (g) Chicken Anemia Agent.

The following examples further illustrate the embodiments of the present invention.

EXAMPLE I

Reovirus 2177 Pathogenicity

A. Characterization in broilers

1. Characterization by inoculating broilers via three routes a. Procedure

In vivo characterization of the eleven isolates referred to above was conducted by inoculating 1-day-old chickens by the intra-abdominal, intracerebral and footpad routes.

b. Results

Several of the isolates were found to be highly pathogenic by all routes producing significant mortality characterized by liver damage including necrosis, inflammation, hemorrhage and perihepatitis. Pericarditis was not uncommon in birds that survived for two weeks or longer. Other isolates varied in pathogenicity with only one virus (2177) being relatively apathogenic.

These results are shown in Table 1.

TABLE 1

Pathogenicity of several avian reoviruses for 1-day old commercial broiler chickens when inoculated[1] by various routes.

| Reovirus Inoculum | Mortality (No. Dead/Total) | | | Foot Pad Lesions No. Affected/Total |
|---|---|---|---|---|
| | Intracerebral | Intra-abdominal | Footpad | |
| 2177 | 0/10 | 0/10 | 0/10 | 3/10 |
| 2035 | 0/10 | 1/10 | 2/10 | 10/10 |
| 2408 | 6/10 | 6/10 | 6/10 | 10/10 |
| 1733 | 10/10 | 9/10 | 8/10 | 10/10 |

[1]Each bird was inoculated with approximately $10^4$ Embryo Lethal Dose 50 of each virus.

2. Weight depression, mortality and antibody production a. Procedure

To further characterize the above reovirus isolates in vivo, the viruses were inoculated into 1-day-old and 2-week-old broiler chickens by more natural routes of exposure (oral and intratracheal). Weights, mortality and antibody production were monitored for several weeks following inoculation.

b. Results

The results supported the original classification that 2177 was relatively apathogenic. The most pathogenic virus isolates produced higher mortality rates (Table 2), lower average body weights (Table 3), and induced a more consistent antibody response than reovirus 2177 (Table 4). In contrast, the mortality and mean body weights in chickens injected with

TABLE 2

Trial 1. Total mortality of broiler chickens during a 7-week period following oral and intratracheal inoculation with different reovirus isolates ($10^{3.5}$ $ELD_{50}$/bird) at 1 day or 2 weeks of age.

| Reovirus isolate | Age | No. dead/total | % Mortality |
|---|---|---|---|
| None | 1 day | 1/25 | 4 |
| | 2 wk | 1/25 | 4 |
| S1133 | 1 day | 1/25 | 4 |
| | 2 wk | 2/25 | 8 |
| 2177 | 1 day | 1/25 | 4 |
| | 2 wk | 1/25 | 4 |
| 2035 | 1 day | 2/25 | 8 |
| | 2 wk | 1/25 | 4 |
| 2408-2 | 1 day | 6/25 | 24 |
| | 2 wk | 1/25 | 4 |
| 1733 | 1 day | 21/25 | 84 |
| | 2 wk | 0/25 | 0 |

TABLE 3

Trial 1. Mean body weights (grams) ± standard deviations during a 7-week period following oral and intratracheal inoculation of broilers at 1 day or 2 weeks of age with different reovirus isolates ($10^{3.5}$ $ELD_{50}$/bird).

| Reovirus isolate | Inoculated | Age of birds[A] | | | |
|---|---|---|---|---|---|
| | | 2 weeks | 4 weeks | 6 weeks | 7 weeks |
| None | 1 day | 302 ± 29.2 | 931 ± 101.9 | 1831 ± 270.0 | 2238 ± 420.4 |
| | 2 wk | 228 ± 26.7 | 858 ± 93.9 | 1670 ± 202.1 | 1946 ± 404.3 |
| S1133 | 1 day | 313 ± 39.6 | 917 ± 123.3 | 1659 ± 224.7* | 2049 ± 327.1* |
| | 2 wk | — | 877 ± 47.9 | 1561 ± 188.6 | 1964 ± 161.9 |
| 2177 | 1 day | 290 ± 25.2 | 882 ± 105.5 | 1744 ± 253.1 | 2220 ± 295.2 |
| | 2 wk | — | 863 ± 91.0 | 1771 ± 222.6 | 2233 ± 300.5 |
| 2035 | 1 day | 314 ± 37.2 | 929 ± 132.1 | 1754 ± 281.3 | 2048 ± 309.8* |
| | 2 wk | — | 899 ± 106.1 | 1772 ± 230.2 | 2118 ± 278.6 |
| 2408 | 1 day | 232 ± 64.7* | 628 ± 186.5* | 1214 ± 330.3* | 1549 ± 380.6* |
| | 2 wk | — | 874 ± 80.8 | 1722 ± 166.9 | 2065 ± 213.0 |
| 1733 | 1 day | 252 ± 20.6* | 595 ± 150.2* | 1070 ± 349.0* | 1342 ± 416.9* |
| | 2 wk | — | 884 ± 97.6 | 1712 ± 204.3 | 2108 ± 252.6 |

[A]Values followed by an asterisk were significantly different from uninoculated controls ($P < 0.05$).

2177 was equivalent to the mortality and the mean body weights of the controls. In addition, the serum antibody response in chickens injected with 2177 was less consistent than the antibody response in chickens injected with the more virulent isolates. This experiment and results were reported in Rosenberger et al. Avian Dis. 33:535–544 (1989).

TABLE 4

Trial 1. Reovirus precipitating serum antibody in chickens after oral and intratracheal inoculation with reovirus ($10^{3.5}$ ELD$_{50}$/bird) at 1 day or 2 weeks of age

| Reovirus isolate | Inoculation | Age of birds (wks) when bled | | | | | | |
|---|---|---|---|---|---|---|---|---|
| | | 1 | 2 | 3 | 4 | 5 | 6 | 7 |
| S1133 | 1 day | 0/5[A] | 0/5 | 1/5 | 1/5 | 1/5 | 1/5 | 4/5 |
| | 2 wk | — | 0/4 | 0/4 | 0/4 | 0/4 | 0/3 | 1/3 |
| 2177 | 1 day | 0/5 | 0/5 | 2/5 | 4/5 | 0/5 | 2/4 | 0/4 |
| | 2 wk | — | 0/5 | 0/5 | 0/5 | 0/5 | 0/5 | 1/4 |
| 2035 | 1 day | 0/5 | 0/5 | 0/5 | 4/5 | 4/5 | 3/5 | 2/4 |
| | 2 wk | — | 0/5 | 0/5 | 0/5 | 0/5 | 0/5 | 0/5 |
| 2408 | 1 day | 0/3 | 2/3 | 2/3 | 2/3 | 2/3 | 3/3 | 2/3 |
| | 2 wk | — | 0/5 | 0/5 | 0/5 | 0/5 | 0/5 | 1/5 |
| 1733 | 1 day | 0/4 | 4/4 | 2/4 | 4/4 | 4/4 | 4/4 | 4/4 |
| | 2 wk | — | 0/5 | 1/5 | 2/5 | 1/4 | 2/4 | 4/4 |

[A]Number of birds with antibody/total number bled.

3. Tissue tropism and histopathology
   a. Procedure
      The tissue tropism and subsequent histopathology of infected tissues also indicated that 2177 was apathogenic compared to the other isolates. One-day-old broiler chickens were inoculated with the different reovirus isolates via the oral and intratracheal route. At 4, 7, 10 and 14 days post-inoculation (PI) chickens from each inoculum group were killed, and sections of the pancreas, liver, trachea, gastrocnemius tendon, and three areas of the intestine were collected for virus isolation and histopathological evaluation.
   b. Results
      The results indicated that the more virulent isolates, 1733 and 2408, could be isolated from all tissues throughout the 14-day sampling period. The 2177 isolate was recovered from the liver, trachea and intestine at day 7 PI, but at day 10 and 14 virus isolation was inconsistent. The 2177 isolate was not isolated from the tendon at any time (see Table 5). The histopathological evaluation of these tissues indicated that all of the reovirus isolates except 2177 caused microscopic lesions (Table 6). Isolate 2177 was omitted from the table since no microscopic lesions were seen in chickens inoculated with this isolate.

TABLE 5

Trial 2. Reovirus reisolations following oral and intratracheal inoculation of 1-day-old broilers with different reovirus isolates ($10^{3.5}$ ELD$_{50}$/bird).

| Reovirus isolate | Days PI | Tissues[A] | | | | |
|---|---|---|---|---|---|---|
| | | Liver | Trachea | Intestine | Pancreas | Tendons |
| S1133 | 4 | + | + | + | + | − |
| | 7 | + | + | + | − | − |
| | 10 | + | + | + | − | + |
| | 14 | − | − | + | − | + |
| 2177 | 4 | − | + | + | − | − |
| | 7 | + | + | + | − | − |
| | 10 | + | − | − | − | − |
| | 14 | − | − | + | − | − |
| 2035 | 4 | + | + | + | − | − |
| | 7 | + | + | + | − | − |
| | 10 | + | + | + | − | − |
| | 14 | + | − | − | − | − |
| 2408 | 4 | + | N.S. | + | − | + |
| | 7 | + | + | + | + | + |
| | 10 | + | + | + | + | + |
| | 14 | + | + | + | + | + |
| 1733 | 4 | + | + | + | + | + |
| | 7 | + | + | + | + | + |
| | 10 | + | + | + | + | + |
| | 14 | + | + | + | + | + |

[A]+ = virus isolated; − = no virus isolated; N.S. = no sample.

TABLE 6

Trial 2. Liver and intestinal lesions of broilers inoculated orally and intratracheally with different reovirus isolates ($10^{3.5}$ ELD$_{50}$/bird) at 1 day of age.

| | Lesion score[A] | | | | | | | | | | | |
|---|---|---|---|---|---|---|---|---|---|---|---|---|
| | 7 days PI | | | | 10 days PI | | | | 14 days PI | | | |
| Tissue and lesions | S1133 | 2035 | 2408 | 1733 | S1133 | 2035 | 2408 | 1733 | S1133 | 2035 | 2408 | 1733 |
| Liver | | | | | | | | | | | | |
| Focal necrosis | − | − | ++ | +++ | − | − | − | − | − | − | − | − |
| Lymphoid cell infiltration | − | − | ++ | +++ | − | − | − | − | − | − | − | − |
| Vacuolated hepatocytes | − | − | ++ | +++ | − | − | + | + | − | − | − | − |
| Hepatocyte regeneration | − | − | ++ | + | − | − | + | + | − | − | − | − |
| Lymphoid follicular hyperplasia | + | − | ++ | + | − | − | +++ | +++ | − | − | ± | ± |
| Focal hemorrhage | − | − | − | + | − | − | − | − | − | − | − | − |
| Intestine | | | | | | | | | | | | |
| Atrophic intestinal villi | ++ | +++ | ++ | ++ | + | − | − | − | − | ++ | − | − |
| Hypertrophy of crypt | + | − | + | + | − | − | − | − | − | − | − | − |
| Lymphocyte infiltration | ++ | +++ | + | ++ | − | − | − | − | − | − | − | − |

TABLE 6-continued

Trial 2. Liver and intestinal lesions of broilers inoculated orally and intratracheally with different reovirus isolates ($10^{3.5}$ $ELD_{50}$/bird) at 1 day of age.

| | Lesion score[A] | | | | | | | | | | | |
|---|---|---|---|---|---|---|---|---|---|---|---|---|
| | 7 days PI | | | | 10 days PI | | | | 14 days PI | | | |
| Tissue and lesions | S1133 | 2035 | 2408 | 1733 | S1133 | 2035 | 2408 | 1733 | S1133 | 2035 | 2408 | 1733 |
| Pancreas | | | | | | | | | | | | |
| Hyperplastic lymphoid tissue | − | − | − | − | − | − | +++ | − | − | − | − | − |
| Pancreatitis | − | − | − | − | − | − | ++ | − | − | − | − | +++ |
| Tendon Tenosynovitis | − | − | − | − | +++ | − | +++ | ++ | +++ | − | ++ | +++ |

[A] − = negative (no change); ± = very slight change; + = slight change; ++ = moderate change; +++ = severe change.

EXAMPLE II

Characterization of 2177 in SPF leghorns

1. Characterization by inoculating leghorns via three different routes a. Procedure The in vivo characterization of reovirus 2177 was also conducted in SPF leghorns. This was done by preparing a series of dilutions of reoviruses 2177, 2035, S1133, 2408, and 1733 and inoculating chickens at 1-day of age by the oral, intratracheal, or footpad routes. The chickens were observed for differences in footpad inflammation, mortality, and weight depression.

b. Results

1). Footpad inflammation

The results indicated that the amount of virus needed to cause footpad inflammation was very small. For all isolates except 2177, less than 1.0 log base 10 Embryo Lethal Dose (ELD) 50 was needed to induce inflammation. Reovirus 2177 needed 2.2 log base 10 ELD 50 to cause inflammation (see Table 7).

2). Mortality

The mortality results in chickens indicated that the only route of inoculation that caused a consistent pattern of mortality was the footpad route of inoculation. The results indicated that 2177 was apathogenic since no deaths occurred in chickens inoculated with high concentrations of the virus (4.3 log base 10 ELD 50). With other reovirus isolates, the chicken lethal dose 50% ranged form 1.6 to 3.7 log base 10 ELD 50 (see Table 8).

3). Weight reduction

Depressed growth rates occurred in chickens inoculated via the intratracheal and footpad routes. In the orally inoculated chickens, only the highest concentration of 1733 caused weight depression. The most severe weight depression occurred in chickens inoculated via the footpad route. Reovirus isolates 2408 and 1733 caused as much as 26% weight reduction at <0.7 and 1.0 log base 10 ELD 50, respectively. Isolates 2035 and S1133 also caused weight depression. Isolate 2177 did not cause weight depression at any virus concentration tested (see Table 9).

TABLE 7

Dose of reovirus ($log_{10}$ $ELD_{50}$) inoculated into the footpad of SPF leghorns at 1-day of age which caused inflammation in 50% of the birds.

| REOVIRUS | VIRUS DOSE[1] |
|---|---|
| 2177 | 2.2 |
| 2035 | <0.2 |
| S1133 | <1.0 |
| 1733 | <1.0 |
| 2408 | <0.7 |

[1]$Log_{10}$ $ELD_{50}$ calculated by the Reed and Muench (1938) method.

TABLE 8

Dose of reovirus ($log_{10}$ $ELD_{50}$) inoculated into SPF leghorns by the footpad route at 1-day of age causing mortality in 50% of the birds.

| REOVIRUS | VIRUS DOSE[1] |
|---|---|
| 2177 | NM[2] |
| S1133 | NM |
| 2035 | 3.7 |
| 1733 | 2.5 |
| 2408 | 1.6 |

[1]$Log_{10}$ $ELD_{50}$ calculated by the Reed and Muench (1938) method.
[2]NM = no mortality occurred in birds inoculated with high doses of 2177 (4.3 $ELD_{50}$) or S1133 (4.0 $ELD_{50}$).

TABLE 9

Depressed growth rates (percent reduction in weight) at 2-wk of age in SPF leghorns inoculated at 1-day of age by different routes with various doses of reovirus pathotypes.

| REOVIRUS | | ROUTE OF INOCULATION | | |
|---|---|---|---|---|
| ISOLATE | DOSE[1] | ORAL | INTRA-TRACHEAL | FOOTPAD |
| 2177 | 4.3 | NONE[2] | NONE | NONE |
| 2035 | 4.2 | NONE | NONE | 19.6 |
| | 3.2 | NONE | 19.7 | 14.2 |
| | 2.2 | NONE | 11.9 | 29.9 |
| | 1.2 | NONE | NONE | 16.9 |
| S1133 | 4.0 | NONE | 16.2 | NONE |
| | 3.0 | NONE | 14.3 | 12.1 |
| | 2.0 | NONE | 14.6 | NONE |
| | 1.0 | NONE | NONE | NONE |
| | <1.0 | NONE | NONE | 18.2 |
| 2408 | 2.7 | NONE | NONE | 20.4 |
| | 1.7 | NONE | NONE | 36.6 |

TABLE 9-continued

Depressed growth rates (percent reduction in weight) at 2-wk of age in SPF leghorns inoculated at 1-day of age by different routes with various doses of reovirus pathotypes.

| REOVIRUS | | ROUTE OF INOCULATION | | |
|---|---|---|---|---|
| ISOLATE | DOSE[1] | ORAL | INTRA-TRACHEAL | FOOTPAD |
| | 0.7 | NONE | NONE | 32.8 |
| | <0.7 | NONE | 12.2 | 26.1 |
| 1733 | 4.0 | 18.8 | 11.6 | ALL DIED |
| | 3.0 | NONE | 11.0 | 24.3 |
| | 2.0 | NONE | NONE | 31.7 |
| | 1.0 | NONE | NONE | 26.7 |
| | <1.0 | NONE | NONE | 17.3 |

[1]Virus dose ($\log_{10}$ ELD$_{50}$) inoculated into 5 birds per route resulting in at least a 10% weight reduction.
[2]Percent weight reduction compared to uninoculated control birds.

2. Tissue tropism and histopathology studies of 2177 infection in SPF leghorns
   a. Procedure
   Three reovirus isolates; 2177, 2035 and 1733 were used to inoculate 1-day-old SPF leghorns via the intratracheal (IT) route. At various time post-inoculation, three chickens from each virus group were bled and sacrificed for the collection of thymus (th), trachea (tr), liver (li), intestine (in), cecal tonsil (ct), spleen (sp), bursa (bu) tendon (te), red blood cells (RBC), white blood cells (WBC), and plasma (p). Tissues were processed for virus isolation and histopathology.
   b. Results
   1). Gross lesions and mortality The appearance of gross lesions at necropsy and the percent mortality was greatest in chickens inoculated with 1733 (see Table 10). Both 1733 and 2035 displayed signs of infection and mortality whereas in the 2177 inoculated group, no specific mortality or lesions were observed.

2). Virus isolation
The virus isolation results from chickens inoculated at 1-day of age with the three pathotypes indicated that 1733 was the most virulent as indicated by the large number of tissues infected (see Table 11). On the other hand, 2177 was avirulent as the virus was reisolated primarily from the cecal tonsils.

3). Persistence
The highly virulent isolate, 1733, was demonstrated to persist the longest. Virus could be recovered at 22 weeks PI from the tendons of chickens. Isolate 2035 was also observed to persist in the tendon, but for only 49 days PI. Isolate 2177 was not found in the tendon at any time and was only found in the cecal tonsils until 28 days of age.

4). Microscopic lesions
Selected tissues (thymus, liver, spleen, bursa and tendon) that were positive for virus isolation were also evaluated for microscopic lesions. The lesions that were observed in these infected tissues and the lesion scoring system are described in Table 12. The severity of these lesions depended on the isolate (see Table 13). Isolate 1733 appeared to be more virulent than the other isolates as indicated by moderate lesions in the thymus and severe lesions in the spleen, bursa, and tendon. The severity of 2035 was much less and 2177 did not cause microscopic lesions.

TABLE 10

Mortality and gross lesions at necropsy in SPF leghorns for 22 weeks following inoculation at 1-day of age with $10^{3.5}$ ELD$_{50}$ of each reovirus pathotype of the intratracheal route.

| Reovirus | Mortality | Gross Lesions[1,3] | | | | | | | |
|---|---|---|---|---|---|---|---|---|---|
| | | LN | SPM | PC | HP | PH | AS | FHN | TE |
| 2177 | 5/45* | —[2] | — | — | — | — | — | — | — |
| 2035 | 3/45 | 2/45 | — | — | — | — | 1/45 | — | — |
| 1733 | 14/60 | 15/60 | 11/60 | 2/60 | — | 3/60 | 8/60 | 5/60 | 4/60 |
| None | 1/15* | — | — | — | — | — | — | — | — |

[1]Gross lesions: LN = liver necrosis, SPM = splenomegaly, PC = pericarditis, HP = hydropericardium, PH = perihepatitis, AS = sir sacculitis, FHN = femoral head necrosis, TE = edematous tendon or swollen hock.
[2](—) = no lesions observed.
[3]Number of chickens affected over the total number of inoculated chickens per reovirus isolate.
*Mortality due to non-specific causes since no lesions were observed.

TABLE 11

Virus isolations from tissues of SPF leghorns inoculated by the intratracheal route with $10^{3.5}$ ELD$_{50}$ of avian reovirus pathotypes at 1-day of age.

| Time Post- | Reovirus | | |
|---|---|---|---|
| Inoculation | 2177 | 2035 | 1733 |
| 12 hr | NV[1] | NV | NV |
| 24 hr | NV | tr, li, sp | NV |

TABLE 11-continued

Virus isolations from tissues of SPF leghorns inoculated by the intratracheal route with $10^{3.5}$ ELD$_{50}$ of avian reovirus pathotypes at 1-day of age.

| Time Post-Inoculation | Reovirus 2177 | 2035 | 1733 |
|---|---|---|---|
| 3 day | bu | NV | tr, li, ct, sp, bu |
| 7 day | ct | tr, li, sp[2] | th, tr, li, in, ct, sp, bu, te, wbc, p |
|  |  | ct | th, tr, li, in, ct, sp, bu, te |
|  |  | th, li, in, ct, sp, bu, te | th, tr, li, ct, sp |
| 14 day | ct | ct | tr, li, sp, bu, te |
|  | ct | ct | th, in, sp, te, wbc |
|  | ct | ct, sp | th, tr, li, in, ct, sp, bu, te |
| 21 day | ct | ct | li, ct, sp, bu |
|  | ct | ct, bu | li, sp, te |
|  |  | sp, te | ct, sp, bu |
| 28 day | ct | ct | te |
|  |  |  | ct |
|  |  |  | ct, bu |
| 35 day | NV | ct | ct, te |
|  |  | ct |  |
| 42 day | NV | te | te |
| 49 day | NV | te | NV |
| 56 day | NV | NV | NV |
| 22 wk | NV(0/9) | NV(0/12) | te(5/18) |

[1]Abbreviations: th = thymus, tr = trachea, li = liver, in = intestine, te = tendon, ct = cecal tonsil, sp = spleen, bu = bursa, wbc = white blood cell, p = plasma, NV = no virus, hr = hours, wk = weeks.
[2]Each line represents the results, when isolations were made, from one bird. Three birds were sampled for each time PI except at 22 wk where the number of positive isolations is shown over the total number of birds sampled.

TABLE 12

Descriptions of the microscopic lesions observed in tissues from which virus was reisolated. The tissues were removed at necropsy from SPF leghorns which were inoculated with $10^{3.5}$ ELD$_{50}$ of reovirus pathotypes at 1-day of age by the intratracheal route.

| Tissues | Severity | Microscopic Lesions |
|---|---|---|
| All tissues | − | No lesions |
| Th | + | Mild lymphocyte depletion, slight cortical thinning |
| Th | ++ | Lymphocyte depletion in both cortex and medulla, cortex thinning |
| Li | + | Swollen hepatocytes and dilated sinusoids, mild fibrosis of the capsule |
| Sp | + | Slight depletion around periarterial sheaths |
| Sp | ++ | Cellular depletion, possible edema |
| Sp | +++ | Severe cellular depletion, areas of coagulated protein |
| Bu | + | Slight follicular lymphoid depletion |
| Bu | ++ | Follicular lymphoid depletion and thinning |
| Bu | +++ | Severely depleted follicles, heterophil rings present |
| Te (A)[2] | + | Inflammation with presence of few heterophils, tendon degeneration |
| Te (A) | ++ | Inflammation with presence of heterophils and macrophages, tendon degeneration |
| Te (A) | +++ | Inflammation with excessive infiltration of heterophils and macrophages, tendon degeneration |
| Te(S) | + | Inflammation with presence of few heterophils and lymphocytes, tendon degeneration |
| Te(S) | ++ | Inflammation with presence of large numbers of heterophils and lymphocytes, tendon degeneration |
| Te(S) | +++ | Inflammation with excessive infiltration of heterophils and lymphocytes, tendon degeneration, tendon sheath thickening |
| Te(C) | + | Inflammation with presence of few lymphocytes |
| Te(C) | ++ | Inflammation with lymphocytes and plasma cells, tendon sheath thickening |
| Te(C) | +++ | Inflammation with excessive infiltration of lymphocytes, plasma cells, Russell bodies; synovial membrane proliferation, tendon sheath thickening |

[1]Abbreviations: Th = thymus, Li = Liver, Sp = spleen, Bu = bursa, Te = tendon
[2]Tendon lesions: (A) = acute, (S) = subacute, (C) = chronic

TABLE 13

Microscopic lesions observed in tissues from which reovirus was reisolated. The tissues were removed at necropsy from SPF leghorns inoculated at 1-day of age by the intratracheal route with $10^{3.5}$ $ELD_{50}$ of reovirus pathotypes.

| Time post-inoculation | 2177 | 2035 | | | | 1733 | | | | |
|---|---|---|---|---|---|---|---|---|---|---|
| | Bu[1] | Li | Sp | Bu | Te | Th | Li | Sp | Bu | Te |
| 24 hr | ND[2] | –[3] | + | ND | ND | ND | ND | ND | ND | ND |
| 3 days | – | ND | ND | ND | ND | ND | – | ++ | – | ND |
| 7 days | ND | – | + | + | – | ++ | – | +++ | ++ | ++ |
| 14 days | ND | ND | – | ND | ND | + | + | + | +++ | +++ |
| 21 days | ND | ND | – | – | ND | ND | – | – | – | ++ |
| 28 days | ND | ND | ND | ND | ND | ND | ND | ND | ND | + |
| 35 days | ND | ND | ND | ND | ND | ND | ND | ND | ND | +++ |
| 42 days | ND | ND | ND | ND | – | ND | ND | ND | ND | + |
| 49 days | ND | ND | ND | ND | + | ND | ND | ND | ND | ND |
| 22 weeks | ND | ND | ND | ND | ND | ND | ND | ND | ND | +++ |

[1]Tissues collected from 3 chickens at each time post-inoculation: Th = thymus, Li = liver, Sp = spleen, Bu = bursa, Te = tendon.
[2]ND = Not done. Only tissues positive for virus reisolation were evaluated for microscopic lesions.
[3]Please refer to Table 12 for the lesion scoring system.

3. Immunosuppression studies of 2177 in SPF leghorns
   a. Procedure
   SPF leghorns were inoculated at 1-day of age with either 2177, 2035, or 1733 by the IT route. A mitogen stimulation assay was performed on peripheral blood lymphocytes (PBL) collected at 7- and 21-days of age.
   b. Results
   Seven days after inoculation of leghorns at 1-day of age with isolate 1733, a significant depression in the ability of the PBL to undergo blastogenic transformation was observed (see Table 14). PBL collected from chickens showed a stimulation index of only 38.0 while PBL from the uninoculated controls as well as 2177 and 2035 showed similar and significantly higher stimulation indices ranging from 84.4 to 116.9.

At 21 days after inoculation, PBL from chickens showed that the depressive effect of 1733 was no longer observed and no immunosuppression was observed in the 2035 or the 2177 inoculated chickens.

EXAMPLE III

Molecular Characterization

Avian reoviruses have a genome consisting of ten segments of double-stranded RNA (dsRNA). Biochemical characterization has demonstrated that significant differences exist in the migration patterns of the double-stranded segments among different isolates. See Gouvea and Schnitzer, *J. Virology*, 43:465–471 (1982), incorporated herein by reference.

Cytoplasmic RNA from infected cells was extracted as described by Sharpe and Fields (*J. Virology* 38:389–392, 1981). Polyacrylamide gel electrophoresis (PAGE) was carried out in slab gels in a discontinuous Tris-glycine buffer system as described by Cross and Fields (*J. Virology*, 19:162–173, 1976). Radioautography was performed by exposing X-Omat film (Kodak) to the dried gel at –70° C.,

TABLE 14

The response of peripheral blood lymphocytes isolated from SPF leghorns at 7 and 21 days after inoculation at 1-day of age by the intratracheal route with $10^{3.5} ELD_{50}$ of reovirus pathotypes as measured by in vitro tritiated thymidine uptake following PHA-P stimulation.

| | Mitogen Stimulation Response | | | | | |
|---|---|---|---|---|---|---|
| | Day 7 | | | Day 21 | | |
| Reo- | CPM Range[1] | | | CPM Range | | |
| virus | +PHA | –PHA | SI[2] | +PHA | –PHA | SI |
| None | (13)[3] 2173–15039 | 20–146 | 108.8 ± 1.2 a[4] | (16) 1817–23423 | 22–83 | 220.3 ± 1.3 b |
| 2177 | (13) 1464–14373 | 22–113 | 84.4 ± 1.3 a | (16) 2268–15703 | 20–78 | 180.2 ± 1.2 b |
| 2035 | (12) 1563–29210 | 19–119 | 116.9 ± 1.3 a | (16) 4919–31066 | 22–92 | 402.1 ± 1.2 a |
| 1733 | (13) 362–11628 | 20–195 | 38.0 ± 1.3 b | (15) 3625–17624 | 20–54 | 253.91.2 ab |

[1]CPM: Range of counts per minute with PHA or without PHA for each reovirus isolate.
[2]SI: Mean stimulation index ± SEM calculated by dividing the CPM with PHA by the CPM without PHA for each sample and then determining the mean of the SI's for each isolate.
[3]Number in parentheses indicates the number of birds tested.
[4]Different letters indicate a statistically significant difference (p < 0.05) between virus treatments according to a 1-way analysis of variance using the GLM procedure.

and developing was done by standard photographic techniques.

A fairly large number of different avian reovirus isolates were available from Connecticut and Delaware and represented field samples collected over a several-year period. In addition, reovirus isolates from other areas within the United States, England, Scotland, and Germany and prototype Japanese strains were also analyzed. From these data, it appears that those viruses isolated from within the same geographic area were most alike with respect to their dsRNA migration patterns. However, isolate 2177 had a migration pattern strikingly different from that of other isolates obtained within the same geographic area. As far as is known, the bird infected with 2177 originated from a breeding stock similar to that of birds infected by other isolates. In addition, no birds from outside the immediate geographic vicinity had been recently introduced.

In particular, the M2 RNA band migrated more slowly and the S3 RNA band migrated more quickly than the same RNA bands from all other isolates obtained from the same geographical region.

EXAMPLE IV

Minimal Protective Dose Study of Live Reovirus Vaccine

The purpose of this study was to demonstrate the efficacy of reovirus isolate 2177 at product passage when inoculated into one-day-old SPF chickens via the subcutaneous (SC) route. For this study and studies of the vaccines that follow, the master seed was prepared by 14 passages in CEF, followed by 5-6 passages in chicken embryos. The so-called product passage was obtained by an additional 4 passages in cell culture (CEF).

One hundred sixty one-day-old chicks were divided into three equal groups of 40 birds each and two groups of 20 birds each and placed into stainless steel, negative pressure isolator units. Groups containing 40 birds each were inoculated by the SC route with 0.1 ml. of inoculum (reovirus strain 2177 prepared in chicken embryo fibroblasts at the fourth passage above master seed virus and diluted in tryptose phosphate broth) to give approximately 2.5, 3.0 and 3.5 log base 10 $TCID_{50}$ dose of 2177 per chicken. One group of 40 birds was used per dosage. The two groups containing 20 birds each were placed together in one isolator to serve as non-vaccinated, non-challenged controls and as non-vaccinated, challenged controls.

At three weeks post-vaccination all chickens were moved into a colony house. The vaccinates and one group of non-vaccinates were challenged with 0.1 ml. of the S1133 challenge virus via the footpad route (the challenge virus was the U.S.D.A. S1133 challenge, diluted 1:10,000 in TPB). The non-vaccinated, non-challenged controls remained unchallenged.

Footpad readings taken on day 6 through day 14 post-challenge were used to determine the percent protection. Readings taken on day 4 and day 5 were not used since swelling that occurs within 5 days post-reovirus challenge is considered as nonspecific. A cumulative footpad inflammation score for each chicken for the 9 day period was determined.

The mean and standard deviation of the footpad swelling of the non-vaccinated, challenged controls were used to determine protection. A chicken was determined to be protected if its footpad inflammation cumulative value was less than the mean of the footpad inflammation of the non-vaccinated, challenged controls minus two standard deviations.

The results of this study are set forth in Table 15 below. The data indicate that the lowest dose of reovirus 2177 used in this trial, 2.5 log base 10 $TCID_{50}$ per dose, is efficacious in chickens challenged at three weeks post-vaccination with S1133 challenge virus, as determined by footpad inflammation. The data also suggests that the minimal protective dose of reovirus 2177 may be lower than 2.5 log base 10 $TCID_{50}$, since 100% of the chickens vaccinated with this dose were protected.

TABLE 15

Minimal protective dose of reovirus 2177 MSV + 4 020491 in SPF leghorn chickens vaccinated at 1-day of age by the SC route and challenged at 3 weeks of age.

| Vaccine | Dose | Age at Challenge | # Protected[1]/ total | % Protected | Average Group Footpad Score |
| --- | --- | --- | --- | --- | --- |
| 2177 | 2.5 | 3 wks | 40/40 | 100.0 | 0.8 ± 1.6 |
| 2177 | 2.9 | 3 wks | 40/40 | 100.0 | 1.1 ± 1.7 |
| 2177 | 3.4 | 3 wks | 40/40 | 100.0 | 0.6 ± 1.2 |
| None | — | 3 wks | 0/20 | 0.0 | 17.4 ± 3.7 |
| None | — | — | 19/19 | 100.0 | 0.0 ± 0.0 |

[1]A chicken was determined to be protected if its footpad swelling cumulative value was less than the mean swelling of the challenge control minus two standard deviations [17.4 − (2 × 3.7) = 10.0].

EXAMPLE V

Reovirus Isolation Challenge Model, Live Reovirus Vaccine

The purpose of this study was to analyze a virus isolation challenge model to demonstrate the efficacy of reovirus isolate 2177 when challenged with a virulent reovirus typically associated with malabsorption syndrome (strain 1733).

Briefly, one-day-old chickens were divided into four groups: groups 1 and 3 were vaccinated with approximately 5.0 log base 10 $TCID_{50}$ 2177 per 0.1 ml. dose via the subcutaneous route (vaccine formulation is as in Example V). The chickens in group 1 were challenged via the intratracheal (IT) route. Group 3 chickens were challenged via the footpad route. Groups 2 and 4 were control groups that remained non-vaccinated. The results are shown in Table 16 below.

The challenge virus was a preparation of reovirus 1733, diluted in TPB to contain approximately 4.0 log base 10 $TCID_{50}$ per 0.1 ml. dose.

The chickens in vaccine groups 1 and 2 were challenged at 16 days of age with 4.0 log base 10 $TCID_{50}$ of reovirus 1733 per 0.1 ml. dose via the intratracheal route. Chickens in vaccination groups 3 and 4 were challenged with the same preparation of challenge 1733 reovirus via the footpad route.

On the day of challenge, 5 chickens from the vaccinates (group 1) and 5 chickens from the non-vaccinated controls (group 2) were sacrificed to collect the spleen for virus isolation. Virus isolated at this time was vaccine virus.

Five days post-challenge, chickens challenged via the IT route (groups 1 and 2) were sacrificed to collect the spleen for virus isolation. Chickens challenged via the footpad route (groups 3 and 4) were observed daily for 5 days starting on day 5 post-challenge for evidence of footpad swelling.

Spleens harvested from chickens were placed into 1 ml. of TPB containing 0.75% neomycin. The tissues were ground with tissue grinders. An additional 1.0 ml. was added to the sample and 0.1 ml. was inoculated into 5-day-old embryonated eggs. The eggs were candled daily for mortality for 10 days. Chorioallantoic membranes were collected from any embryos that died within the 10 day period and tested for reovirus antigen by agar gel precipitation. A tissue was considered positive for reovirus if a line of identity formed between the unknown sample and a positive known reovirus sample.

TABLE 16

Virus isolation results from the spleens harvested from SPF chickens vaccinated at 1-day of age with reovirus 2177 by the SC route and challenged with 1733 at 16 days of age via the intratracheal route.

| Group | Virus | Route | Titer | # Positive pre-chall.[1] | Chall. Route | Protection[2] 5 days PC | % |
|---|---|---|---|---|---|---|---|
| 1 | 2177 | SC | 4.3 logs | 0/5 | IT | 18/20 | 90 |
| 2 | None | — | — | 0/5 | IT | 1/20 | 5 |
| 3 | 2177 | SC | 4.3 logs | — | FP | 10/10 | 100 |
| 4 | None | — | — | — | FP | 1/11 | 9 |

[1]Pre-challenge samples were collected on the day of challenge (16 days post-vaccination).
[2]Virus isolation was conducted buy inoculating spleen tissue collected at 5 days post-challenge into embryonated eggs. Footpads were read on days 5-9 post-challenge.

The purpose of this experiment was to determine if reovirus 2177 could protect chickens when challenged with a reovirus normally associated with malabsorption syndrome, strain 1733, rather than the tenosynovitis challenge strain (S1133). The experiment was designed to use virus isolation from the spleen as a means to determine protection instead of footpad challenge. Virus isolation was performed by inoculating embryonated eggs with ground spleen samples and testing the chorioallantoic membrane for reovirus antigen in an agar gel precipitation test.

The results indicated that 90% of the vaccinated chickens tested with the virus isolation technique were protected compared to 100% protection in the chickens challenged via the footpad route. In the non-vaccinated controls, 95% of the chickens tested with the virus isolation method were found to be susceptible, compared with 91% of the chickens tested with the footpad inflammation method.

The results of this study demonstrate two points: (1) the virus isolation technique can be used to determine protection in chickens vaccinated with reovirus strain 2177 and challenged with a reovirus malabsorption strain 1733 instead of the tenosynovitis strain S1133, and (2) the 2177 vaccine provides protection to chickens when challenged with the malabsorption 1773.

EXAMPLE VII

Interference Study of Reovirus Strain 2177 with HVT/SB-1 Vaccination

The purpose of this study was to determine if reovirus strain 2177 interferes with HVT/SB-1 vaccination efficacy. The design of the experiment is set forth in Table 17 below.

TABLE 17

Experimental design for evaluating the interference of reovirus 2177 with HVT/SB-1 when inoculated via the SC route at 1-day of age in SPF chickens.

| Group | Vaccine | # of birds | Dose | Challenge[1] |
|---|---|---|---|---|
| 1 | None | 51 | None | RB1B |
| 2 | HVT SB-1 | 50 | 6024 PFU 334 PFU | RB1B |
| 3 | 2177 HVT SB-1 | 50 | 3.7 logs 6024 PFU 334 PFU | RB1B |

[1]Challenge was administered via the intra-abdominal route at 5-days post-vaccination.

On the day of vaccination, 2 ampules of HVT and 2 ampules of SB-1 were thawed and resuspended together into 400 ml. Marek's diluent. This mixture was then aliquoted into four 100 ml. aliquots. One aliquot constituted the HVT/SB-1 vaccination group and was set aside. To one of the other aliquots, 1 ml. of reovirus 2177 was added to constitute the 2177/HVT/SB-1 group. The remaining two aliquots were not used.

On the day of vaccination, 10 replicate titrations of the resuspended HVT/SB-1 combination were conducted. Five of these replicate titrations were conducted on primary CEF cells to determine the SB-1 titer and five of these replicate titrations were done on secondary CEF to determine the HVT titer.

The vaccine containing reovirus 2177/HVT/SB-1 was frozen and five replicate titrations of the reovirus 2177 were conducted on primary CEF.

The RB1B strain of Marek's Disease Virus at about 500 plaque forming units per dose was used to challenge the chickens at 5 days of age intra-abdominally. Chickens that died within the first week post-challenge were considered as dying from non-specific causes since Marek's Disease has an incubation period of approximately 3 to 4 weeks before gross lesions and clinical signs of Marek's Disease are observed. These chickens and chickens that died prior to challenge were not included in the protection evaluation. The number of chickens with lesions or that died after this one week post-challenge period was divided by the total number of chickens remaining after the first week post-challenge to determine the percent of chickens protected.

The replicate titrations on each virus indicated that the preparations of the two vaccines contained the following virus titers:

TABLE 18

| Vaccine | Lot # | Titer |
|---|---|---|
| HVT | 18-2068 | 6024 PFU per dose |
| SB-1 | 19-1006 | 334 PFU per dose |
| 2177 | 020491 | 3.7 $TCID_{50}$ per dose |

The protection results indicated that in the HVT/SB-1 vaccinates, 88% of the chickens were protected. In the group vaccinated with 2177/HVT/SB-1, 89% were protected. In the non-vaccinated, challenged controls, 4% of the chickens did not have lesions (see Table 19 below). In other words, the results indicate that the efficacy of an HVT/SB-1 vaccine containing reovirus strain 2177, is no different from the same preparation of HVT/SB-1 without the reovirus 2177. Therefore, reovirus 2177 can be added to HVT/SB-1 vaccines without causing interference with the efficacy of Marek

TABLE 19

Efficacy of HVT/SB-1 when mixed with reovirus 2177 and inoculated into SPF leghorns via the SC route at 1-day of age and challenged at 5-days of age via the intra-abdominal route with the RB1B challenge.

| Vaccine | Dose | # of birds | Nonspecific[1] deaths | # protected/ # inoculated[2] | % |
|---|---|---|---|---|---|
| None | None | 51 | 3 | 2/48 | 4 |
| HVT SB-1 | 6024 PFU 334 PFU | 50 | 2 | 42/48 | 88 |
| 2177 HVT SB-1 | 3.7 logs 6024 PFU 334 PFU | 50 | 3 | 42/47 | 89 |

[1]Deaths occurring before or within 1 week post-challenge were considered nonspecific.
[2]# inoculated = the number of chickens initially inoculated minus the number of nonspecific deaths.

Studies were also conducted on whether the HVT/SB-1 vaccine interfered with the efficacy of the 2177 vaccine. Results indicated that when a vaccine was prepared containing 4.2 log base 10 $TCID_{50}$ per dose of reovirus 2177, 5636 PFU HVT, and 5733 PFU SB-1 per dose, there was no effect on the efficacy of the reovirus 2177 vaccine. The percent protection of the combination vaccine was 93% compared to 100% protection when reovirus 2177 was used alone.

We claim:

1. An isolated avian reovirus having all of the identifying characteristics of reovirus strain 2177 which is deposited at the ATCC under accession number VR 2449.

2. A vaccine comprising the avian reovirus of claim 1.

3. A combination vaccine, comprising the avian reovirus of claim 1 and at least one Marek's Disease vaccine.

4. The combination vaccine of claim 3, wherein the at least one Marek's Disease vaccine is selected from the group consisting of SB-1, HVT and CVI 988.

5. The combination vaccine of claim 3, wherein the at least one Marek's Disease vaccine is selected from the group consisting of SB-1 and HVT.

6. A combination vaccine, comprising the avian reovirus of claim 1 and an Infectious Bursal Disease Virus vaccine.

7. A combination vaccine, comprising the avian reovirus of claim 1 together with at least one Marek's Disease vaccine and at least one Infectious Bursal Disease Virus vaccine.

8. A combination vaccine, comprising the avian reovirus of claim 1, Newcastle Disease Virus vaccine, Infectious Bronchitis Virus vaccine, Marek's Disease vaccine and at least one Infectious Bursal Disease Virus vaccine.

9. A combination vaccine, comprising the avian reovirus of claim 1, together with a vaccine or vaccines of one or more viruses selected from the group consisting of Avian Encephalomyelitis, Fowl Pox and Chicken Anemia Agent.

10. A method of immunizing chickens against avian reovirus infection, comprising administering an effective amount of a vaccine comprising the reovirus of claim 1.

11. The method of claim 10, wherein the vaccine further comprises an effective amount of at least one Marek's Disease vaccine.

12. The method of claim 10, wherein the at least one Marek's Disease vaccine is selected from the group consisting of SB-1, HVT and CVI 988.

13. The method of claim 12, wherein the at least one Marek's Disease vaccine is selected from the group consisting of SB-1 and HVT.

14. The method of claim 10, wherein the vaccine further comprises an effective amount of an Infectious Bursal Disease Virus vaccine.

15. The method of claim 10, wherein the vaccine further comprises at least one Marek's Disease vaccine and at least one Infectious Bursal Disease Virus vaccine.

16. The method of claim 10, wherein the vaccine further comprises Newcastle Disease Virus vaccine and Infectious Bronchitis Virus vaccine.

17. The method of claim 10, wherein the vaccine further comprises a vaccine or vaccines of one or more viruses selected from the group consisting of Avian Encephalomyelitis, Fowl Pox and Chicken Anemia Agent.

* * * * *